US00PP09265P

United States Patent [19]

Preil et al.

[11] Patent Number: Plant 9,265

[45] Date of Patent: Aug. 29, 1995

[54] RHODODENDRON RHODUNTER 10

[75] Inventors: Walter Preil, Amersbek; Rainer Ebbinghaus, Ahrensburg, both of Germany

[73] Assignee: Inkarho Pflanzenvertrieb GmbH+Co. KG, Giesselhorst, Germany

[21] Appl. No.: 160,576

[22] Filed: Dec. 1, 1993

[51] Int. Cl.[6] ..... A01H 5/00

[52] U.S. Cl. ..... Plt./55

[58] Field of Search ..... Plt. 55, 56

[56] References Cited

U.S. PATENT DOCUMENTS

P.P. 2,508 5/1965 Shammarello ..... Plt./55

P.P. 7,457 2/1991 Mossholder ..... Plt./56

*Primary Examiner*—James R. Feyrer

*Attorney, Agent, or Firm*—Collard & Roe

[57] ABSTRACT

The new plant is a new and distinct cultivar of a rhododendron used as a rootstock, and characterized by a plant height (of the original plant) of 1.0 m, with a plant width of 1.2 m in 13 years; a habit of broad bush, very compact; an annual terminal growth of mature plants being about 10–15 cm and for young plants being 20–25 cm; a flowering period in the first week of May to the third week of May; a flower color being white (R.H.S. Colour Chart 155 D) with green tinge and faint yellow-brown markings (nearly 164 B–173 A according to R.H.S. Colour Chart); 10 stamens of very striking brown color with a green stigma and stamens much longer than style; leaf shape being small and elliptical, 6–9 cm long and 1.5–3.5 cm broad, with a dark green upper surface and light green lower surface; hardy to a temperature down to −26° C., or −10° F.

1 Drawing Sheet

BACKGROUND OF THE INVENTION

The present invention relates to a new and distinct cultivar of a rhododendron used as a rootstock. This rootstock, named "Rhodunter 10," tolerates much more lime than all other known rootstocks, for example, "Cunningham's White," "County of York," "Anna Rose Whitney," *R. ponticum,* etc. It grows well in soils having a pH of 6.8–7.0. It is only necessary to take care that the soil is loose enough. Further, this rootstock needs no peat moss, which is a great benefit. This cross-originated by crossing *R. fortunei* "Best Form" (German form) with R. "Cunningham's White."

While this plant might advantageously be used as a rootstock due to its uniquely advantageous characteristic tolerance of sweet soils, it also may be used as an attractive foundation plant or specimen plant in landscape appointments due to its small size and dense canopy at maturity, and due to profuse presentation of unusually pure white, attractive, white blossoms of single form; and by its extended flowering period.

SUMMARY OF THE INVENTION

This new hybrid has the following combination of characteristics which distinguish it from other varieties.

Plant height (of the original plant) of 1.0 m, with a plant width of 1.2 m in 13 years. It has a habit of broad bush, very compact. An annual terminal growth of mature plants is about 10–15 cm, and for young plants is 20–25 cm. It has a flowering period in the first week of May to the third week of May, a flower color of white (R.H.S. Colour Chart 155 D) with green tinge and faint yellow-brown markings (nearly 164 B–173 A according to R.H.S. Colour Chart). There are 10 stamens of very striking brown color, with a green stigma, and stamens much longer than style. The leaf shape is small and elliptical, 6–9 cm long and 1.5–3.5 cm broad, with a dark green upper surface and light green lower surface.

It is hardy to a temperature down to −26° C., or −10° F.

This selection of rhododendron is a seedling selected from a population of 1,700,000 seedlings. This selection resulted from the cross of *Rhododendron fortunei* "Best Form" also known as "German Form" with R. "Cunningham's White". "Rhodunter 10" has been asexually reproduced by me or under my direction through in vitro culture by the Federal Centre for Breeding Research on Cultivated Plants/Institute for Ornamental Plant Breeding, 22926 Ahrensburg, Germany. All clones of "Rhodunter 10" have remained true to type and are identical to the original selection in all distinguishing characteristics.

The breeding is directed to a rhododendron variety which grows best in soil of pH 7 and has a good grafting ability. This variety resulted as a selection from about 1,700,000 seedlings.

In Germany, most of all rhododendrons are graftings for having a better adaptation of soil. The variety "Rhodunter 10" is a rootstock. The difference over other rootstocks is that this new variety is much better in adapting to the soil.

DESCRIPTION OF THE PHOTOGRAPHS

The top photograph shows the terminal portion of a flowering branch in full bloom, and depicts the shape of the single, white flowers formed as well as the reproductive organs of the flowers.

The second photograph illustrates a whole specimen of the claimed plant and shows the color of a mature and current season's foilage after an early season growth flush.

The bottom photograph is a close-up of new growth over the previous season's growth which reflects the leaf colors, leaf shape and leaf stem characteristics of both new and old leaves.

DETAILED PLANT DESCRIPTION

The following is a detailed description of the new variety of rhododendron known as "Rhodunter 10."

Plant:
- *Growth form.*—Wider than tall, Compact and dense.
- *Shape of generative terminal bud.*—Wide elliptical.
- *Scales.*—Missing.
- *Behavior in winter.*—Evergreen.

Young leaf:
- *Color of upper side.*—Middle green.
- *Color of underside.*—About same as the upper side as shown.
- *Hairs on underside.*—Missing.

Mature leaf:
- *Length (including stem).*—Middle to long.
- *Width.*—Narrow to wide.
- *Shape.*—Small elliptical.
- *Color of upper side.*—Dark green.
- *Color of underside.*—Light green.
- *Rims on upper side.*—Missing.
- *Cross section.*—Convex.
- *Rotation.*—Present.
- *Rims on leave stem.*—Missing.

Flower density:
- *Number of blossom.*—High, normally about 13 or more.

Flower stem:
- *Length.*—Long.

Calyx:
- *Present or not.*—Present.
- *Type.*—Simple.

Calyx tip:
- *Length.*—Normal.

Blossom:
- *Circumference.*—Very small to small.
- *Shape.*—Bell shape.
- *Fragrance.*—Absent or very little.
- *Type.*—Simple.
- *Number of flower petals.*—Typically 7, fused, forming a bell-shaped corolla.

Crown tip:
- *Rim waviness.*—Medium.
- *Length of crown tip in relation to blossom length.*—Long.
- *Number.*—Seven.
- *Tip.*—Wide.
- *Color of rim of upper side.*—White (about RHS Colour Chart 155D) with shade of green.
- *Color of middle of upper side.*—White (about RHS Colour Chart 155D).
- *Color of middle of underside.*—White (about RHS Colour Chart 155D).
- *Color of rim of underside.*—White (about RHS Colour Chart 155D) with shade of green.

Blossom throat:
- *Markings.*—Faint.
- *Type of markings.*—Points, flowing into each other.
- *Color of markings.*—Yellow-brown (about RHS Colour Chart 164 B to 173 A).
- *Color in comparison to upper side of crown tip middle.*—Darker.

Anthers:
- *Number.*—Ten.
- *Conspicuousness.*—Conspicuous.
- *Color.*—Brown.

Pistil:
- *Color of stigma.*—Green.
- *Anther length.*—Sigma superior to anther.

Blossom:
- *Time of flowering.*—Very early to early.

Similar varieties and differences to these varieties:

| Name of similar variety | Characteristic in which the similar variety is different | Degree of marks of similar variety | Degree of marks of variety of application |
|---|---|---|---|
| Cunningham's White | Blossom Circumference<br>Leaf Rotation | small to medium<br>missing | very small to small<br>present |

Additional information: HCC means Horticultural Colour Chart, 1941. RHS means R.H.S. Colour Chart 1986. Publisher: Flower Council of Holland, Leiden.

We claim:

1. A new and distinct variety of rhododendron plant used as rootstock, as shown and described, characterized by a plant height, of the original plant, of 1.0 m, with a plant width of 1.2 m in 13 years; a habit of broad bush, very compact; an annual terminal growth of mature plants being about 10–15 cm, and for young plants being 20–25 cm; a flowering period in the first week of May to the third week of May; a flower color of white, R.H.S. Colour chart 155D, with green tinge and faint yellow-brown markings, nearly 164 B–173 A according to R.H.S. Colour Chart; 10 stamens of very striking brown color, with a green stigma and stamens much longer than style; leaf shape being small and elliptical, 6–9 cm long and 1.5–3.5 cm broad, with a dark green upper surface and light green lower surface; and being hardy to a temperature down to −26° C., or −10° F.

* * * * *

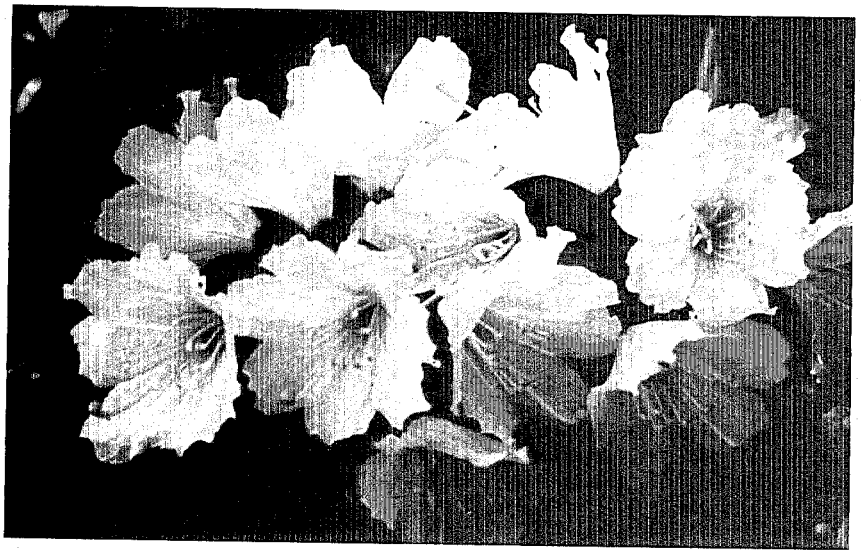
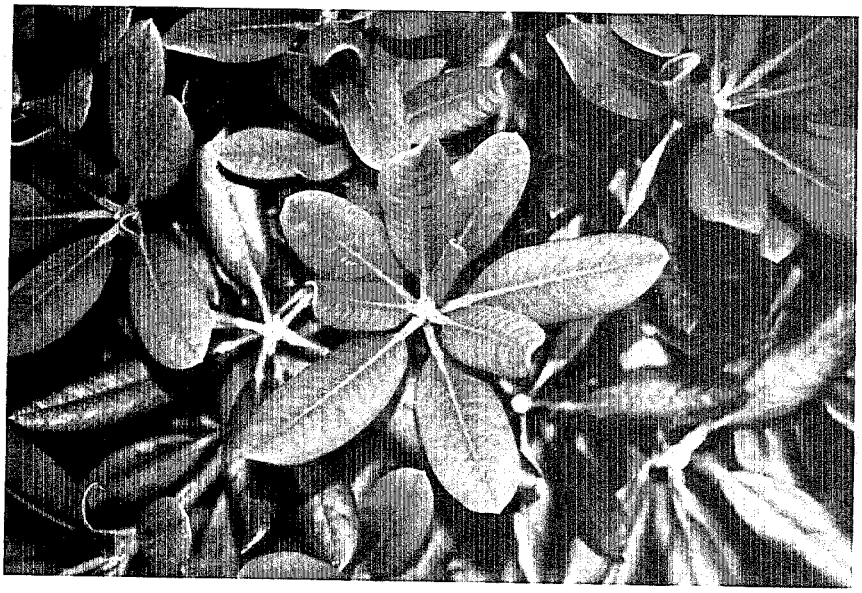
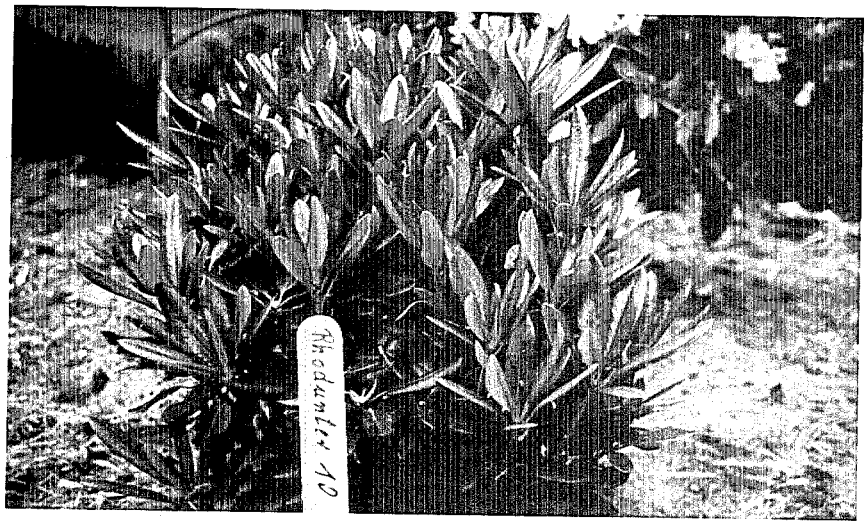
Rhodanthe 10